United States Patent
Henry et al.

(10) Patent No.: US 8,491,524 B2
(45) Date of Patent: *Jul. 23, 2013

(54) NEEDLELESS INJECTOR DRUG CAPSULE AND A METHOD FOR FILLING THEREOF

(75) Inventors: William Henry, Trumpington (GB); Andrew Lewis, Trumpington (GB)

(73) Assignee: Zogenix, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/495,390

(22) Filed: Jun. 13, 2012

(65) Prior Publication Data

US 2012/0253273 A1    Oct. 4, 2012

Related U.S. Application Data

(63) Continuation of application No. 10/496,357, filed as application No. PCT/GB02/05220 on Nov. 21, 2002, now Pat. No. 8,241,243.

(30) Foreign Application Priority Data

Nov. 21, 2001 (GB) .................................. 0127942.1

(51) Int. Cl.
*A61M 5/30* (2006.01)
*A61M 37/00* (2006.01)

(52) U.S. Cl.
USPC ................. 604/68; 604/70; 604/72; 604/131; 604/141

(58) Field of Classification Search
USPC ................ 428/410, 428; 604/68, 70, 72, 131, 604/141
See application file for complete search history.

(56) References Cited

U.S. PATENT DOCUMENTS

| 3,650,084 A | 3/1972 | Moreland |
| 3,688,765 A | 9/1972 | Gassaway |
| 3,773,487 A | 11/1973 | Plumat et al. |
| 3,985,535 A | 10/1976 | Bennett et al. |
| 4,156,455 A * | 5/1979 | van der Meulen ............ 165/292 |
| 4,156,755 A | 5/1979 | Rinehart |
| 4,376,153 A | 3/1983 | Cardy |
| 4,380,505 A * | 4/1983 | Wittenhorst .................... 261/20 |
| 4,397,669 A | 8/1983 | Haisma et al. |
| 4,670,417 A | 6/1987 | Iwasaki et al. |
| 4,740,402 A | 4/1988 | Maeda et al. |
| 4,927,433 A | 5/1990 | Wieland et al. |
| 5,182,274 A | 1/1993 | Makino et al. |
| 5,485,496 A | 1/1996 | Lee et al. |
| 5,707,996 A | 1/1998 | Parinello |
| 5,891,086 A | 4/1999 | Weston |
| 6,216,493 B1 | 4/2001 | Weston et al. |
| 6,251,091 B1 | 6/2001 | Weston |
| 6,415,631 B1 | 7/2002 | Weston et al. |
| 6,673,038 B2 | 1/2004 | Weston |
| 2001/0004682 A1 | 6/2001 | Weston |
| 2003/0079744 A1* | 5/2003 | Bonney et al. ........... 128/203.12 |

FOREIGN PATENT DOCUMENTS

| JP | Hei-10-509613 | | 9/1998 |
| JP | 2001-511037 | | 8/2001 |
| WO | WO 96/15821 | * | 5/1996 |
| WO | WO 98/31409 | | 7/1998 |

* cited by examiner

*Primary Examiner* — Michael G Hartley
*Assistant Examiner* — Jagadishwar Samala
(74) *Attorney, Agent, or Firm* — Karl Bozicevic; Bozicevic, Field & Francis LLP

(57) ABSTRACT

A method for filling needleless injector capsules with liquid drug, whereby dissolved gas within the drug is replaced by a less soluble gas in order to reduce the inclusion of gas bubbles, or to prevent the growth of bubbles during storage and thereby prevent breakage of the capsules.

15 Claims, 6 Drawing Sheets

NEEDLELESS INJECTOR DRUG CAPSULE AND A METHOD FOR FILLING THEREOF

CROSS-REFERENCE

This application is continuation application of Ser. No. 10/496,357, filed Jun. 4, 2007, which application claims the benefit of priority to International Application Serial No. PCT/GB02/05220 filed Nov. 21, 2002 (now publication No. WO 03/045479) which application claims the benefit of priority to GB 0127942.1 filed Nov. 21, 2001, all of which are incorporated herein by reference in their entirety noting that the current application controls to the extent there is any contradiction with any earlier applications and to which applications we claim priority under 35 USC §120.

BACKGROUND OF THE INVENTION

Needleless injectors are used as an alternative to needle-type hypodermic injectors for delivering liquid drugs and other substances through the skin and into the underlying tissues. The drug is dispensed from a drug capsule having a piston which is driven with sufficient force that the drug is expelled at sufficiently high pressure to pierce the skin. Typically, the drug capsule will comprise a hollow cylindrical chamber with a discharge orifice at one end, and a piston slidingly and sealingly located at the other. The piston is caused to move towards the orifice to dispense the drug by a ram, powered by a variety of means such as a spring, pressurised gas or pyrotechnic charge. The orifice diameter can vary from about 0.08 mm to about 0.7 mm, according to the application.

The more successful and controllable injectors employ a two-phase injection pressure profile; the first is a short but very high pressure pulse to puncture the skin and the second is at a lower pressure to dispense the drug through the hole thus formed. Typically, the first pressure pulse will be of around 100 microsecond duration, and have a peak pressure of 300-500 bar, and the second will last for around 200 milliseconds with a pressure of around 100 bar. The duration of the second phase will vary according to the volume to be delivered.

It is highly preferred that the drug capsule is transparent, so that the contents may be checked for accuracy and contamination. This requirement has placed a severe limitation on the types of materials that may be used, because the transparent material must be strong enough to withstand the extremely high pressures, and must not adversely affect the drug. As a consequence, virtually all of the needleless injectors proposed use a plastic drug capsule, typically made from polycarbonate. However, such materials are generally unsuitable for storing the drug, because they absorb water from the drug, or are permeable to oxygen, or react in some way with the drug. Therefore, drug capsules made from plastics are required to be filled immediately before use, a rather inconvenient procedure, with risk of inaccurate filling and contamination, and requiring training of the operators.

The only material with a long history of satisfactory drug storage is borosilicate glass, but this is very brittle and hence there have been few injectors with glass capsules. The obvious problem with glass capsules is that particles of glass are ejected if they burst. The underlying causes of the weakness of glass capsules are tiny flaws which occur during manufacture, such as scratches, and cracks through incorrect control of temperatures.

The "Intraject" manufactured by Weston Medical Limited is a pre-filled single-use disposable needleless injector, having one of the very few glass capsules suitable for long term drug storage. This is a borosilicate drug capsule of up to 1 ml capacity, made to exceedingly close manufacturing specifications, and further improved by ion exchange strengthening. The breakage rate for these capsules is exceptionally low, but it is desirable to reduce this still further.

Several attempts have been made to reduce the breakage rate for these capsules. For example, further layers of material have been added to the capsule to provide increased physical strength (see international patent publication WO96/15821 in the name of Weston Medical Limited). However, this approach increases significantly the manufacturing costs of the capsule. An alternative approach has been to reduce the number of flaws in the material of the drug capsule, particularly around the discharge orifice. One method of doing this has been to manufacture the capsule without an orifice and then use a laser to drill precisely the orifice (see international patent publication WO01/58638 in the name of Weston Medical Limited). Despite these advances, there is still a requirement for further reducing the incidence of breakages.

SUMMARY OF THE INVENTION

Accordingly, the present invention provides a needleless injector drug capsule containing a liquid drug wherein the liquid drug has been purged by an inert gas having a low solubility in the liquid drug.

Surprisingly, it has been found that the presence of small bubbles of gas previously in solution encourage breakages in the drug capsule and that removal or reduction of these solute gases by purging with a gas having a low solubility reduces the incidence of breakages.

The capsule is preferably made from borosilicate glass, and which may have undergone ion exchange strengthening.

Preferably the inert gas has a solubility of 0.5 to 25 $cm^3$ in 100 $cm^3$ of the liquid drug.

Preferably the inert gas is one or more of helium, argon, neon, krypton, xenon, nitrogen, one or more chlorofluorocarbons and/or one or more hydrofluorocarbons and particularly preferably helium.

In another embodiment of the invention, a needleless injector drug capsule is provided containing a liquid drug wherein the liquid drug has been purged by a gas having a substantially constant solubility in the liquid drug over a range of temperatures corresponding to the storage temperatures for the liquid drug. This range of temperatures may be 0° C. to 30° C.

In another embodiment the present invention provides a method for filling a needleless injector drug capsule with a liquid drug, the method comprising purging the liquid drug with an inert gas having a low solubility in the liquid drug, and filling the capsule.

Preferably the purging process is carried out at a temperature corresponding to the lowest solubility of the inert gas in the liquid drug.

Preferably the inert gas is helium and the purging process is then carried out at 25° C. to 35° C.

Preferably, prior to contact with the liquid drug, the inert gas is forced through a filter having apertures of not more than 0.2 μm.

The liquid drug is preferably stirred during purging.

In another embodiment, the invention provides a method for filling a needleless injector drug capsule with a liquid drug comprising purging the liquid drug with a gas having a substantially constant solubility in the liquid drug over a range of temperatures corresponding to the storage temperatures for the liquid drug.

BRIEF DESCRIPTION OF THE DRAWINGS

Example of the invention, will now be described in detail with reference to the accompanying drawings, in which.

DETAILED DESCRIPTION

Careful investigation of the causes of breakage of the drug capsule has revealed that, in addition to manufacturing flaws in the glass, bubbles of gas (normally air) entrained in the drug may result in the fracture of the capsule. The high initial pressure in the injection cycle causes bubble collapse resulting in localised high stress in the region of the discharge orifice of the capsule (where the bubbles tend to collect). Filling under vacuum will practically eliminate the bubbles of air present in the liquid drug at the time of filling, but dissolved gas tends to come out of solution during storage. Bubbles of up to 2 µl volume do not appear to cause breakage, but above this, the incidence of breakage rises with increasing bubble size.

The present invention seeks to reduce the evolution of gas bubbles from the drug by replacing the dissolved gas by a gas of low solubility in the liquid drug. Interestingly, the applicant has found that alternative methods of removing dissolved gas, e.g. by applying a vacuum to the liquid or sonication of the liquid do not work for certain drug types. Applying a vacuum, for example, has the drawback of removing volatile components which may be part of the drug, and water, in addition to the dissolved gas: This can result in an unacceptable change in the drug formulation. Sonication results in "hot-spots" in the liquid which can them1ally degrade the drug.

The applicant has found that purging a liquid drug with an inert gas, such as helium (He), effectively displaces dissolved gases, particularly oxygen and nitrogen, and that the drug may then be stored within a drug capsule without the risk of gas bubbles appealing during storage at normal temperatures.

Pre-treatment of the drug product by sparging with low solubility gas species minimises the total mass of dissolved gas. By selecting a sparging gas with a low variation in solubility of the gas in the drug as a function of temperature, the propensity for those gases to come out of solution during temperature cycling is also minimised. Helium is one gas satisfying this condition.

Other gases may be used according to the application such as neon, argon, krypton or xenon. Other inert gases of low solubility may also be used, including nitrogen as well as chlorofluorocarbons and hydrofluorocarbons.

Figure 1:
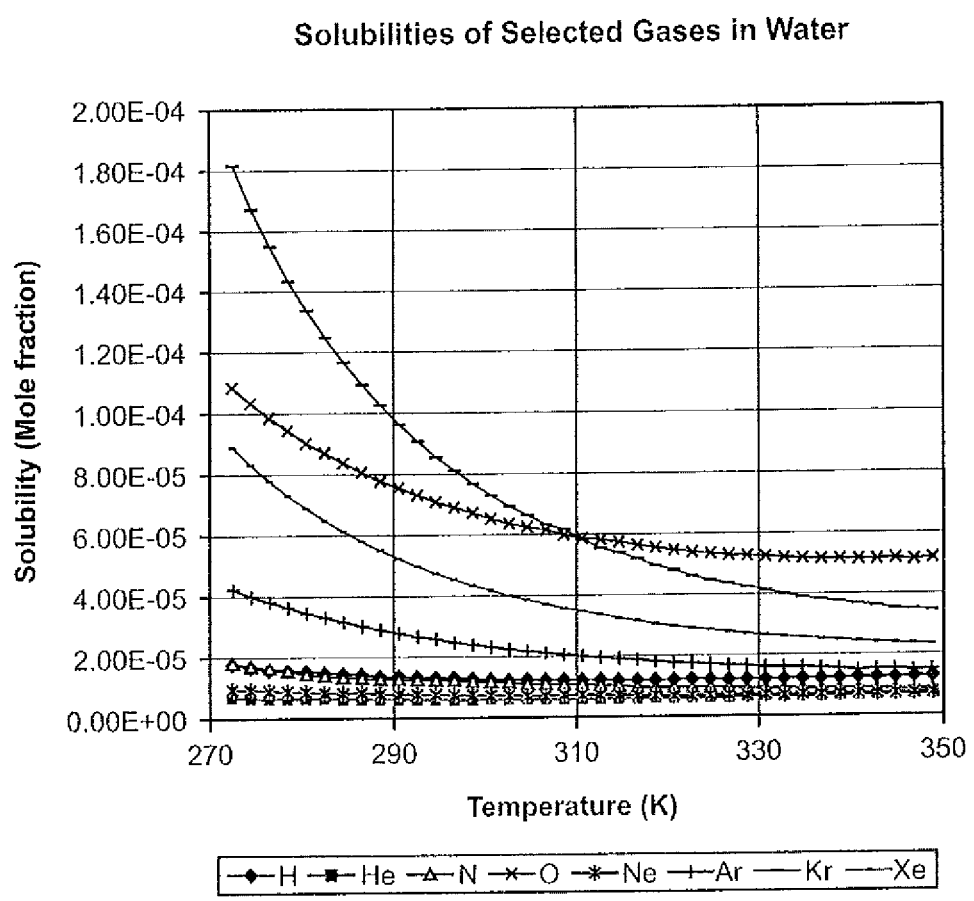
FIG. 1 shows the variation of the solubility of a number of gases in water with temperature.

FIG. 1 shows the solubility of various gases in water over temperature. A flat solubility curve over a range of temperatures corresponding to the temperature range expected during storage will prevent gas coming out of solution during storage.

Plots are shown in FIG. 1 for Hydrogen, Helium, Nitrogen, Oxygen, Neon, Argon, Krypton and Xenon. The storage temperature range may typically be 280° K to 310° K, and a flat solubility curve over this range of temperatures is desired, in addition to low solubility and an "inert" property of the gas. As shown, hydrogen, helium, neon and nitrogen best satisfy the solubility requirements.

The term "inert" used herein denotes a gas which will not react with the liquid drug at normal temperatures and pressures. The term "low solubility" denotes a solubility of the inert gas in the liquid drug which reduces the incidence of bubbles in the liquid drug. Preferably the solubility is from 0.5 to 25 cm$^3$ in 100 cm$^3$ of the liquid drug, preferably 0.9 to 5.0 cm$^3$ in 100 cm$^3$ of the liquid drug and particularly preferably from 0.9 to 1.5 cm$^3$ in 100 cm$^3$ of the liquid drug. Solubility is measured at 25° C. The term "liquid drug" denotes a drug which is liquid at room temperature and pressure, or a drug dissolved or suspended in a solvent, such as water.

A preferred embodiment of the invention is to "sparge" the liquid drug with tiny bubbles of a sparging gas.

Figure 2:
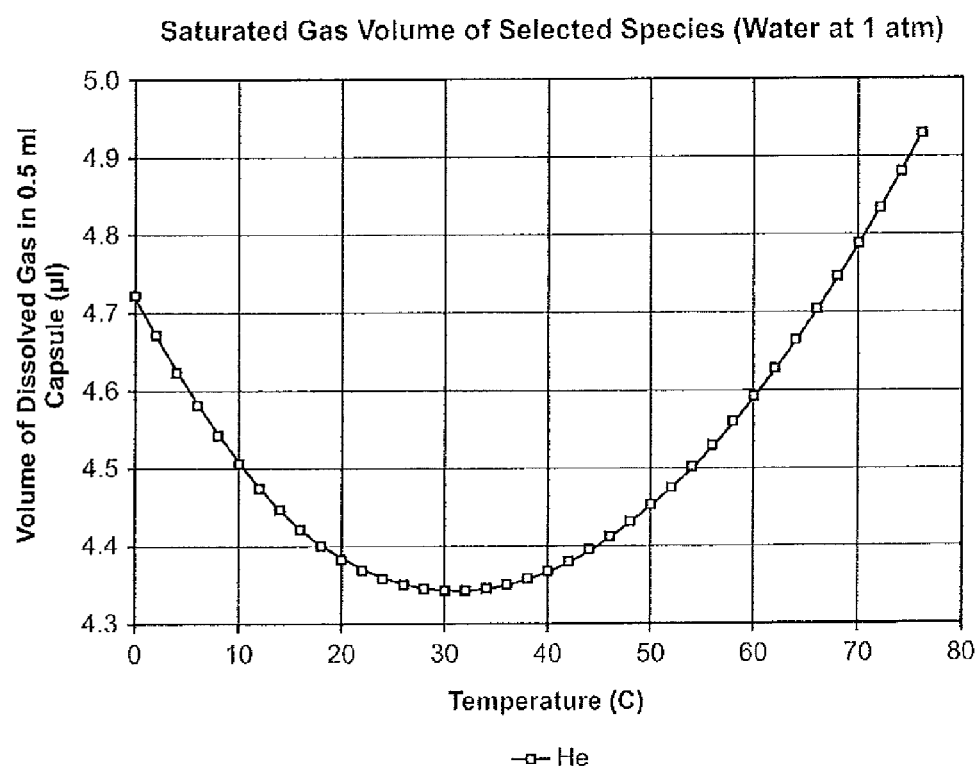
FIG. 2 shows in greater detail the variation of the solubility of helium in water with temperature.

Taking helium as one specific example, FIG. 2 shows that the solubility of helium is at its lowest at approximately 30° C., and wherever the drug is stable at such temperature, it is particularly preferred to conduct the sparging process at this temperature, with a tolerance of about +/−5° C. Preferably, the bubbles may be generated by forcing pressurised helium through a sterile 0.2 micron filter placed in the bottom of a vessel. This produces a very large number of very small bubbles, and after treating, say, 2 liters of an aqueous drug for 15 minutes, the sparging device is removed, and the vessel sealed in a helium (or other gas used for sparging) atmosphere, with minimal over-pressure, until required for the filling of injector capsules.

Obviously, the duration of the treatment will vary according to the volume of liquid, the gas pressure, volume flow rate, and the size and number of the bubbles generated by the sparging device. The gas pressure and volume flow rate are of course linked. Preferably, capsule filling is carried out by first evacuating the capsule to about 0.5 mbar before admitting the drug into the capsule; a full description of a suitable process is disclosed in International patent publication W002/ 060516—"Method for filling needleless injection capsules" in the name of Weston Medical Limited.

It has also been found that stiffing of the liquid during sparging reduces the required sparging time. In particular, it has been found that key input parameters for the control of the sparging process are stirring speed (for example using a magnetic mixer) and the gas flow rate. Increasing the gas flow rate reduces the time required, but there is a maximum practical gas flow rate above which foaming of the drug being sparged is too great. The additional step of stirring reduces further the time required by increasing the time taken for the sparging gas to travel through the liquid, for the same gas flow rate.

In order to monitor the rate at which gas is displaced by the sparging gas, an oxygen probe is used. The air being removed from the drug by sparging is of course almost entirely nitrogen and oxygen, and it has been found that the concentration of dissolved nitrogen and oxygen can be deduced from a measurement of the dissolved oxygen concentration alone.

In order to analyse the effects of the stirring rate and the gas flow rate, a number of experiments were carried out. The table below show the experimental conditions for 5 tests, in which helium was used as the sparging gas. All conditions were equal other than the stirring speed and flow rate. The experiments involved the sparging of 3 liters of solution in a 5 liter Schott glass bottle, with an oxygen probe used to measure (and deduce) the dissolved gas concentrations. In these experiments, the solution contained 0.1% polysorbate 80.

| | Experiment number | | | | | | |
|---|---|---|---|---|---|---|---|
| | 1 | 2 | 3 | 4 | 5 | 6 | 7 |
| Magnetic mixer speed (rpm) | 150 | 150 | 150 | 250 | 350 | 250 | 250 |
| Fine flow meter (ml min$^{-1}$) | 80 | 150 | 190 | 145 | 145 | 150 | 150 |

Figure 3:
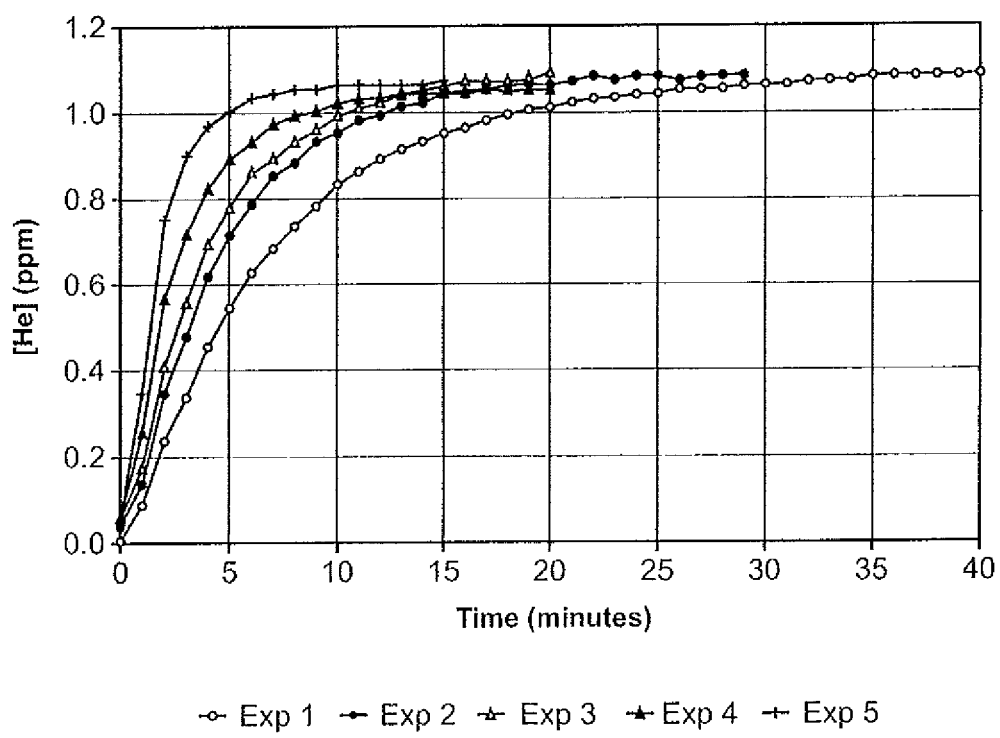
FIG. 3 shows the rate of increase of helium under five different conditions for a sparging method of the invention using helium.

FIG. 3 shows the evolution over time of the helium concentration in the drug. Using best fit techniques, the curves can be. characterised as exponential graphs, each having a characteristic time constant, β.

As there are two sets of three experiments where either the stirrer speed or the flow rate is held constant, it is possible to explore the variation of β as a function of each variable. In both cases, a proportional relationship is found. This suggests that the variables are independent and proportional. From this, it is found that β varies twice as much with stirring speed as with the gas flow rate, so that the stirrer speed is approximately twice as important as the gas flow rate.

Figure 4:
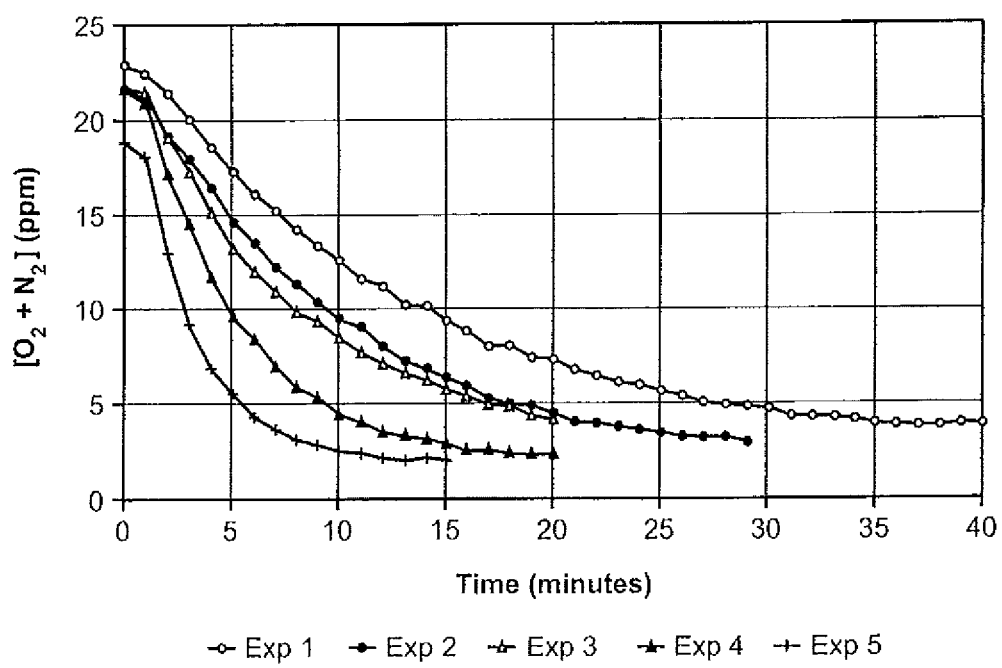
FIG. 4 shows the rate at which nitrogen and oxygen are displaced by helium for the five different conditions of FIG. 4.

FIG. 4 shows the concentration of oxygen and nitrogen over time for the five experimental conditions. The decay curves also follow the exponential model and agree with the graphs of FIG. 3.

Figure 5:
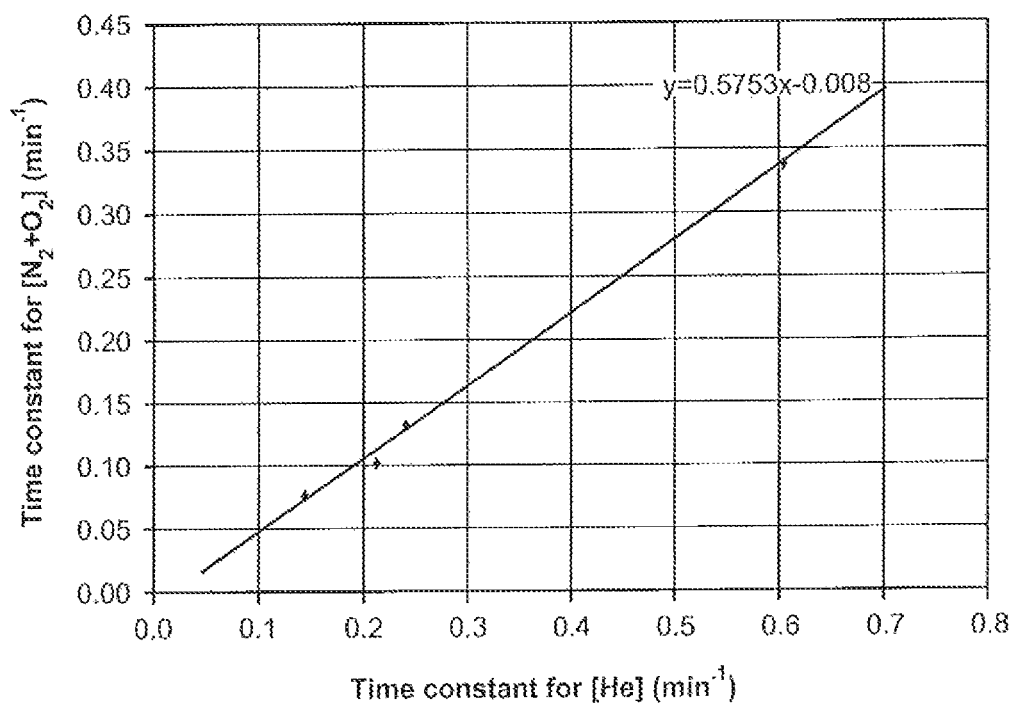
FIG. 5 compares the rate of increase of helium with the rate of decrease of nitrogen and oxygen.
Figure 6:
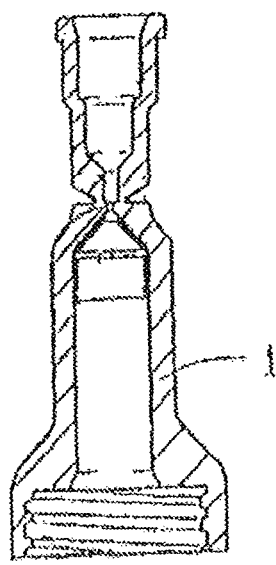
FIG. 6 shows a drug capsule 1 for use with a needle-free drug delivery device. The capsule is being filled in FIG. 6 and is of the type shown within issued U.S. Pat. No. 6,251,091.

It is then possible to compare the time constants for the exponential increase in helium concentration and for the exponential decrease in combined nitrogen and oxygen concentration. FIG. 5 shows this comparison, with the five plotted point representing the five experiments. There is clearly a proportional relationship between the two tin1e constants for different sparging conditions. The constant of proportionality is given as 0.575.

The principal conclusion is that the helium concentration varies at approximately 1.75 times the speed of the combined nitrogen and oxygen concentration. The helium mass transfer process is quicker than the nitrogen and oxygen processes. Selecting the optimum sparging conditions results in operation at the high gas transfer rate portion of the line in FIG. 5.

The sparging operation effectively displaces the dissolved gases in the drug. By selecting the sparging gas to have a flat solubility curve over temperature, the possibility of gas coming out of solution during storage is minimised. As a result, the capsule can be formed from a material which is impermeable to the sparging gas, as there is no need to discharge the sparging gas. For example, a borosilicate glass capsule is selected partly for its impermeability to oxygen, which prevents deterioration of the stored drug. Such a capsule is also impermeable to nitrogen. However, nitrogen can still be used as a sparging gas, particularly if the sparging conditions are selected to correspond to the minimum solubility of nitrogen.

Thus, although examples are given for sparging conditions with helium, the invention is not restricted to helium, and other gases suitable for sparging have been identified.

As can be seen from the experiments above, a preferred stirring speed is in the range 100 rpm to 300 rpm, preferably 200 rpm to 300 rpm.

Other modifications will be apparent to those skilled in the art.

The invention claimed is:

1. A needle free injector drug capsule, comprising:
a container comprised of borosilicate glass strengthened with ion exchange; and
a liquid formulation in the container, wherein the liquid formulation is comprised of a drug, and the liquid formulation has been purged by an inert gas having a solubility of 0.5 cm$^3$ to 25 cm$^3$ in 100 cm$^3$ of the liquid formulation;
wherein the inert gas solubility in the formulation is such that gas does not come out of solution during storage over a range of temperatures of 0° C. to 30° C.

2. A needle free injector drug capsule as claimed in claim 1, wherein the inert gas is selected from the group consisting of helium, argon, neon, krypton, xenon, nitrogen, a chlorofluorocarbon, a hydrofluorocarbon, and a mixture thereof.

3. A needle free injector drug capsule as claimed in claim 2, wherein the inert gas does not include helium.

4. The needle free injector drug capsule as claimed in claim 1, wherein the inert gas is helium.

5. A needle free injector drug capsule, comprising:
a container comprised of glass strengthened with ion exchange; and
a liquid formulation in the container, wherein the liquid formulation is comprised of a drug, and the liquid formulation has been purged by an inert gas soluble in the liquid formulation.

6. The needle free injector drug capsule of claim 5, wherein the inert gas solubility in the formulation over a range of temperatures from 0° C. to 30° C. is such that the inert gas does not come out of solution during temperature cycling.

7. A needle free injector drug capsule as claimed in claim 6, wherein the inert gas is selected from the group consisting of helium, argon, neon, krypton, xenon, nitrogen, a chlorofluorocarbon, a hydrofluorocarbons, and a mixture thereof.

8. A needle free injector drug capsule as claimed in claim 7, wherein the inert gas is helium.

9. The needle free injector drug capsule of claim 5, wherein the inert gas solubility in the formulation is such that gas does not come out of solution during storage over a range of temperatures of from 0° C. to 30° C. and the glass is borosilicate glass.

10. A needle free injector drug capsule, comprising:
a container comprised of glass strengthened with ion exchange; and
a liquid formulation in the container, wherein the liquid formulation is comprised of a drug.

11. The needle free injector drug capsule of claim 10, wherein the liquid formulation has been purged by an inert gas soluble in the liquid formulation.

12. The needle free injector drug capsule of claim 11, wherein the inert gas solubility in the formulation over a range of temperatures from 0° C. to 30° C. is such that the inert gas does not come out of solution during temperature cycling.

13. The needle free injector drug capsule as claimed in claim 12, wherein the inert gas is selected from the group consisting of helium, argon, neon, krypton, xenon, nitrogen, a chlorofluorocarbon, a hydrofluorocarbon, and a mixture thereof.

14. The needle free injector drug capsule as claimed in claim 13, wherein the inert gas is helium.

15. The needle free injector drug capsule of claim 11, wherein the inert gas solubility in the formulation is such that gas does not come out of solution during storage over a range of temperatures of from 0° C. to 30° C. and the glass is borosilicate glass.

* * * * *